(12) United States Patent
Johnson et al.

(10) Patent No.: US 11,572,327 B2
(45) Date of Patent: *Feb. 7, 2023

(54) PROCESS FOR THE PREPARATION OF 1,1,1,2,2-PENTAFLUOROPROPANE

(71) Applicant: Mexichem Fluor S.A. de C.V., San Luis Potosi (MX)

(72) Inventors: Sheryl Louise Johnson, Cheshire (GB); Stephen Andrew Flaherty, Cheshire (GB); Clive Robert Giddis, Cheshire (GB)

(73) Assignee: Mexichem Fluor S.A. de C.V., San Luis Potosi (MX)

( * ) Notice: Subject to any disclaimer, the term of this patent is extended or adjusted under 35 U.S.C. 154(b) by 0 days.

This patent is subject to a terminal disclaimer.

(21) Appl. No.: 17/497,071

(22) Filed: Oct. 8, 2021

(65) Prior Publication Data

US 2022/0098131 A1 Mar. 31, 2022

Related U.S. Application Data

(63) Continuation of application No. 16/855,500, filed on Apr. 22, 2020, now Pat. No. 11,155,506, which is a
(Continued)

(51) Int. Cl.
*C07C 17/20* (2006.01)
*B01J 23/06* (2006.01)
(Continued)

(52) U.S. Cl.
CPC ............. *C07C 17/206* (2013.01); *B01J 23/06* (2013.01); *B01J 23/26* (2013.01); *C07C 17/25* (2013.01); *C07C 19/08* (2013.01); *C07C 21/18* (2013.01)

(58) Field of Classification Search
CPC ..... C07C 17/087; C07C 17/206; C07C 17/25; C07C 21/18; C07C 19/10; C07C 19/08; C07C 19/01
See application file for complete search history.

(56) References Cited

U.S. PATENT DOCUMENTS 2,931,840 A 4/1960 Marquis
9,346,724 B2 5/2016 Lei et al.
(Continued)

FOREIGN PATENT DOCUMENTS

CN 104151131 A 11/2014
EP 0502605 1/1992
(Continued)

OTHER PUBLICATIONS

International Search Report for corresponding International Application No. PCT/GB2016/052133, dated Sep. 27, 2016, 3 pgs.
(Continued)

*Primary Examiner* — Jafar F Parsa
(74) *Attorney, Agent, or Firm* — Crowell & Moring LLP

(57) ABSTRACT

The present invention provides a process for preparing 1,1,1,2,2-pentafluoropropane (245cb), the process comprising gas phase catalytic dehydrochlorination of a composition comprising 1,1,1-trifluoro-2,3-dichloropropane (243db) to produce an intermediate composition comprising 3,3,3-trifluoro-2-chloro-prop-1-ene ($CF_3CCl=CH_2$, 1233$xf$), hydrogen chloride (HCl) and, optionally, air; and gas phase catalytic fluorination with hydrogen fluoride (HF) of the intermediate composition to produce a reactor product composition comprising 245$cb$, HF, HCl and air; wherein the process is carried out with a co-feed of air.

29 Claims, 2 Drawing Sheets

Related U.S. Application Data continuation of application No. 15/745,529, filed as application No. PCT/GB2016/052133 on Jul. 14, 2016, now Pat. No. 10,669,219.

(51) Int. Cl.
*B01J 23/26* (2006.01)
*C07C 17/25* (2006.01)
*C07C 19/08* (2006.01)
*C07C 21/18* (2006.01)

(56) References Cited

U.S. PATENT DOCUMENTS

| | | |
|---|---|---|
| 9,783,471 B2 | 10/2017 | Wendlinger |
| 2009/0240090 A1 | 9/2009 | Merkel et al. |
| 2011/0124930 A1 | 5/2011 | Smith |
| 2011/0160497 A1 | 6/2011 | Deur-Bert et al. |
| 2011/0207975 A9 | 8/2011 | Merkel et al. |
| 2012/0078020 A1 | 3/2012 | Elsheikh et al. |
| 2014/0275649 A1 | 9/2014 | Wang et al. |
| 2014/0275651 A1 | 9/2014 | Wang et al. |
| 2014/0275653 A1 | 9/2014 | Pigamo et al. |
| 2016/0096787 A1 | 4/2016 | Lei et al. |
| 2016/0207855 A1 | 7/2016 | Wendlinger |

FOREIGN PATENT DOCUMENTS

| | | |
|---|---|---|
| EP | 0773061 | 10/1996 |
| EP | 0957074 | 4/1998 |
| EP | 2583959 | 3/2009 |
| WO | WO 98/10862 | 3/1998 |
| WO | WO 2006/106353 | 10/2006 |
| WO | WO 2007/079435 | 7/2007 |
| WO | WO 2008/040969 A2 | 4/2008 |
| WO | WO 2008/054781 | 5/2008 |
| WO | WO 2009/003084 A1 | 12/2008 |
| WO | WO 2009/026526 | 2/2009 |
| WO | WO 2009/125199 | 10/2009 |
| WO | WO 2009/137658 | 11/2009 |
| WO | WO 2009/158321 A1 | 12/2009 |
| WO | WO 2010/116150 | 10/2010 |
| WO | WO 2011/077193 A1 | 6/2011 |
| WO | WO 2011/077394 A1 | 6/2011 |
| WO | WO 2011/087825 | 7/2011 |
| WO | WO 2012/098421 | 7/2012 |
| WO | WO 2012/098422 A1 | 7/2012 |
| WO | WO 2012/115938 | 8/2012 |
| WO | WO 2013/067356 | 5/2013 |
| WO | WO 2013/088195 | 6/2013 |
| WO | WO 2013/111911 | 8/2013 |
| WO | WO 2013/141409 A1 | 9/2013 |
| WO | WO 2014/010750 | 1/2014 |
| WO | WO 2014/025065 | 2/2014 |
| WO | WO 2015/044558 A1 | 4/2015 |

OTHER PUBLICATIONS

Written Opinion for corresponding International Application No. PCT/GB2016/052133, dated Sep. 27, 2016, 5 pgs.

Safetygram 33, "The Hazards of Oxygen and Oxygen-Enriched Mixtures", Air Products and Chemicals, Inc., 2014 (36202); 900-13-101-US, 7 pages.

Health and Safety Executive, "Fire and Explosion Hazards in the Use of Oxygen", HSE8 (rev 2), Reprinted Feb. 2008, 6 pages.

PROCESS FOR THE PREPARATION OF 1,1,1,2,2-PENTAFLUOROPROPANE

RELATED APPLICATIONS

This application is a continuation of patent application Ser. No. 16/855,500 filed 22 Apr. 2020, now U.S. Pat. No. 11,155,506, which is a continuation of patent application Ser. No. 15/745,529 filed 17 Jan. 2018, now U.S. Pat. No. 10,669,219, which is a 371 U.S. National Phase of international application Serial No. PCT/GB2016/052133 filed 14 Jul. 2016, which claims priority from Great Britain Application No. 1512557.8 filed on 17 Jul. 2015, wherein the entire content of each of the aforementioned applications are hereby incorporated by reference herein.

BACKGROUND OF THE INVENTION

The invention relates to a process for preparing 1,1,1,2,2-pentafluoropropane (HFC-245cb, referred to hereinafter as 245cb). In particular, the invention relates to a process for preparing 245cb from 1,1,1-trifluoro-2,3-dichloropropane (HCFC-243db, referred to hereinafter as 243db) via 3,3,3-trifluoro-2-chloro-prop-1-ene (HCFO-1233xf, referred to hereinafter as 1233xf).

SUMMARY OF THE INVENTION

245cb is a useful compound, not least as an intermediate in the preparation of 2,3,3,3-tetrafluoropropene (HFO-1234yf, referred to hereinafter as 1234yf). 245cb is mentioned as an intermediate in the preparation of 1234yf in WO2009/125199. 245cb is also mentioned in passing in other documents concerned with the preparation of 1234yf, such as WO2008/054781, WO2013/111911 and US2014/010750.

The listing or discussion of a prior-published document in this specification should not necessarily be taken as acknowledgment that the document is part of the state of the art or is common general knowledge.

There is a need for an efficient and economic manufacturing process for the preparation of 245cb. The subject invention address this need by the provision of a process for preparing 245cb, the process comprising gas phase catalytic dehydrochlorination of a composition comprising 243db to produce an intermediate composition comprising 1233xf, hydrogen chloride (HCl) and, optionally, air; and gas phase catalytic fluorination of the intermediate composition with hydrogen fluoride (HF) to produce a reactor product composition comprising 245cb, HF, HCl and air; wherein the process is carried out with a co-feed of air.

For the avoidance of doubt, the gas phase catalytic dehydrochlorination comprises conversion of the 243db by dehydrochlorination to 1233xf. Likewise, the gas phase catalytic fluorination comprises conversion of 1233xf to 245cb by fluorination. The conversion of 1233xf ($CF_3CCl=CH_2$) to 245cb ($CF_3CF_2CH_3$) involves the addition of two fluorine substituents and one hydrogen substituent to 1233xf. Put another way, this involves the addition of HF and the replacement of the chlorine substituent with fluorine substituent. Thus, the term fluorination (with HF) in the context of the subject invention can be considered to include combined fluorination and hydrofluorination reactions.

The above process may be carried out batch-wise or continuously. Preferably, the process is carried out continuously. The term "continuously" as use herein is intended to include semi-continuous operation of the process wherein the process is temporarily stopped, for example, to regenerate and/or replace the catalyst used in the catalytic dehydrochlorination of 243db and/or catalytic fluorination of 1233xf. Certain aspects of the invention enable the cycle time between such catalyst regeneration and/or replacement to be lengthened thereby improving the efficiency and economy of the process.

The catalytic dehydrochlorination of 243db and the catalytic fluorination of 1233xf of the process of the invention can be carried out together in a single reactor.

In a preferred aspect, however, the catalytic dehydrochlorination of 243db and the catalytic fluorination of 1233xf are carried out in separate first and second reactors, respectively. Typically, there are advantages associated with the use of separate reactors for these two reactions, including modifying the conditions in each reactor to facilitate the catalytic dehydrochlorination of 243db and the catalytic fluorination of 1233xf, respectively. For example, a higher pressure can be used for the catalytic fluorination of 1233xf compared to the catalytic dehydrochlorination of 243db. Typically, a somewhat higher temperature can be used in the second reactor compared to the first reactor. One reason for such a difference in reactor temperature is the preference for higher temperatures in the second reactor to burn off any catalyst coking. This is explained in more detail later in this specification. The use of two reactors also helps different concentrations of HF and air to be used in the catalytic dehydrochlorination and fluorination reactions.

Whether a single or two reactors are used, any suitable apparatus may be used. Typically, the apparatus is made from one or more materials that are resistant to corrosion, e.g. Hastelloy®, Monel® or Inconel.

Regardless of whether one or two reactors is used, a key feature of the invention is that it is carried out with a co-feed of air. The inventors have surprisingly found that this prevents and/or retards coking of the catalyst or catalysts used in the gas phase catalytic dehydrochlorination of a 243db and/or the gas phase catalytic fluorination of 1233xf (particularly the latter reaction) without significantly impairing conversion and/or selectivity. Put another way, the use of air has been found to significantly reduce the rate of catalyst deactivation in the gas phase transformations of the subject invention. This has the effect of lengthening cycle time, which in turn has benefits of process efficiency and economy. The use of an air co-feed is also believed to enable the process of the invention to be conducted at higher temperatures with a given catalyst. Without being bound by theory, the air co-feed is thought to help burn coke at approximately the same rate at which it is produced, thereby extending cycle time. This is believed to be especially advantageous for the gas phase catalytic fluorination of 1233xf, which compound is fouling to the gas phase fluorination catalyst and relatively difficult to convert to 245cb compared to the typically more facile gas phase catalytic dehydrochlorination of a 243db.

It is believed that it is the oxygen in the air that is primarily responsible for the unexpected effects described in the preceding paragraph. However, there are advantages to using air in the process of the invention rather than oxygen or oxygen enriched air. Use of air (e.g. atmospheric air) is both cheaper than using oxygen or oxygen enriched air. It is also safer to handle air compared to oxygen enriched air or, particularly, oxygen, due to flammability issues. The concentration of oxygen in air (about 21 mol %) is also thought to be especially suitable for use in the process of the invention, in terms of the combination of its effectiveness to prevent and/or retard catalyst coking and its ease of handling. For example, the air, in one embodiment, is compressed and, optionally, dried, prior to feeding to the process of the invention. This handling/processing is considerably safer and more straightforward with air as opposed to oxygen enriched air or, particularly, oxygen.

In a preferred embodiment, the air is supplied from the atmosphere and is dried prior to entering either reactor. The air may be dried by any drying method known in the art, but is preferably compressed and then fed into a drying system comprising a desiccant. Suitable desiccants include silica gel, which can dry the air to a dew point of less than about −40° C. In one aspect there are two or more desiccant chambers so that one can be regenerated whilst the other is drying the air. Alternatively/additionally, the air can be cooled to condense the water.

Typically, the amount of air co-fed to the process of the invention is from about 0.1 to about 500 mol %, based on the amount organics fed and/or present in the reactor(s). By organics we mean the carbon-based compounds present in the process of the invention, particularly 243db, 1233xf and 245cb. In one aspect, the amount of air co-fed to the process of the invention in mol %, as described herein, is based on the amount (i) 243db, (ii) 1233xf, or (iii) the combined amount of 243db and 1233xf. In a preferred aspect, for example wherein the process of the invention is carried out in first and second reactors and the air is co-fed to the second reactor only, the amount of air (mol %) is based on the amount of 1233xf fed to the second reactor.

Preferably, the amount of air co-fed to the process of the invention is from about 1 to about 200 mol %, from about 2 to about 100 mol %, from about 5 to about 100 mol % or from about 10 to about 100 mol %, based on the amount of organics. The preferred amounts of air co-fed to the process of the invention are believed to be limited as follows. If too little air is used, inadequate prevention and/or retardation of coking of the catalyst or catalysts is achieved. If too much air is used, selectivity for the desired products is adversely affected and/or the large quantities of air become more difficult, and therefore expensive, to handle. It is particularly advantageous that the amount of air co-fed to the process is from about 15 to about 95 mol %, preferably from about 20 to about 90 mol %, such as from about 25 to about 85 mol %, based on the amount of organics. These ranges are currently thought to be optimal from the perspective of a combination of ease of handling (e.g. the volume of air to be handled and its effect on the process design) and ability to prevent and/or retard catalyst coking without deleteriously affecting the process chemistry.

When the catalytic dehydrochlorination of 243db and the catalytic fluorination of 1233xf are carried out in separate first and second reactors, respectively, air may be co-fed to the first reactor and/or the second reactor. In one embodiment, air is co-fed to the first reactor and the second reactor, more preferably to the second reactor only.

Thus, the invention provides a process for preparing 245cb, the process comprising gas phase catalytic dehydrochlorination in a first reactor of a composition comprising 243db to produce an intermediate composition comprising 1233xf, HF, HCl; and gas phase catalytic fluorination with HF in a second reactor of the intermediate composition to produce a reactor product composition comprising 245cb, HF, HCl and air; wherein the process is carried out with a co-feed of air to the second reactor.

Whether air is co-fed to the first reactor and the second reactor, or to the second reactor only, the amount of air co fed to the reactor(s) is broadly in accordance with the ranges as defined hereinbefore.

However, when air is co-fed to both the first and second reactors, the amount of air co-fed to the first reactor preferably is less than the amount, on a molar basis, of air co-fed to the second reactor. This is because 1233xf typically is fouling to the gas phase fluorination catalyst in the second reactor and higher concentrations of air are thought to be needed to maintain catalyst stability and activity (e.g. by preventing and/or retarding catalyst coking) in the second reactor compared to the first reactor. Additionally, more forcing conditions may be employed in the second reactor compared to the first reactor in order to achieve the desired levels of 1233xf fluorination conversion and selectivity to 245cb. Higher concentrations of air in the second reactor compared to the first reactor can help maintain catalyst stability and activity under such forcing conditions.

Typically, the amount of air co-fed to the first reactor is less than half the amount co-fed to the second reactor, preferably less than a quarter of the amount of air co-fed to the second reactor, such as less than a tenth of the amount of air co-fed to the second reactor. By way of example, when air is co-fed to both the first and second reactors, the amount of air co-fed to the first reactor typically is from about 0.1 to about 100 mol %, preferably from about 0.2 to about 50 mol %, such as from about 0.3 to about 20 mol %, for example from about 0.4 to about 10 mol %, based on the amount of organics (e.g. based on 243db); whereas the amount of air co-fed to the second reactor typically is from about 1 to about 200 mol %, preferably from about 5 to about 100 mol %, such as from about 10 to about 90 mol %, for example from about 15 to about 85 mol %, based on the amount of organics (e.g. based on 1233xf).

In a preferred embodiment when the catalytic dehydrochlorination of 243db and the catalytic fluorination of 1233xf are carried out in separate first and second reactors, the intermediate composition exiting the first reactor is fed directly to the second reactor. This has the advantage of process economy. For example, when air is co-fed to the first reactor, the intermediate composition contains air. It is preferable, when air is co-fed to the first reactor, for air also to be fed to the second reactor. This can be achieved simply by feeding the intermediate composition exiting the first reactor directly to the second reactor without an intermediate purification step (e.g. to remove air and/or Hel). Is has been found that the presence of HCl does not significantly disadvantage the fluorination of 1233xf. The unexpected benefit of this is the intermediate composition exiting the first reactor can be fed directly to the second reactor without removing HCl, which removal requires energy to cool the composition, remove HCl and re-heat the composition. Of course, even when feeding the intermediate composition exiting the first reactor directly to the second reactor without an intermediate purification step, it may be desirable to heat or cool the intermediate composition, for example if the fluorination reaction in the second reactor is being carried out at a higher temperature than the dehydrochlorination reaction in the first reactor. In the embodiment wherein the intermediate composition is fed directly to the second reactor, it is preferable to have an additional co-feed of air into the second reactor because, as explained above, higher concentrations of air in the second reactor compared to the first reactor can help prevent and/or retard catalyst coking.

The catalyst used in the catalytic dehydrochlorination step may be any suitable catalyst that is effective to dehydrochlorinate 243db. Preferred catalysts are bulk form or supported catalysts comprising activated carbon, a zero-valent metal, a metal oxide, a metal oxyhalide, a metal halide, or mixtures of the foregoing.

For the avoidance of doubt, by bulk form or supported catalysts, catalysts comprising activated carbon, a zero-valent metal, a metal oxide, a metal oxyhalide, a metal halide, or mixtures of the foregoing, we include catalysts that are essentially only bulk form or supported catalysts, catalysts comprising activated carbon, a zero-valent metal, a metal oxide, a metal oxyhalide, a metal halide, or mixtures thereof, and such catalysts that are modified, for example, by the addition of one or more promoters or excipients. Suitable promoters include metals (e.g. transition metals) and/or compounds thereof, and suitable excipients include binders and/or lubricants.

By "activated carbon", we include any carbon with a relatively high surface area such as from about 50 to about 3000 m$^2$ or from about 100 to about 2000 m$^2$ (e.g. from about 200 to about 1500 m$^2$ or about 300 to about 1000 m$^2$). The activated carbon may be derived from any carbonaceous material, such as coal (e.g. charcoal), nutshells (e.g. coconut) and wood. Any form of activated carbon may be used, such as powdered, granulated and pelleted activated carbon. Activated carbon which has been modified (e.g. impregnated) by the addition of Cr, Mn, Au, Fe, Sn, Ta, Ti, Sb, Al, Co, Ni, Mo, Ru, Rh, Pd and/or Pt and/or a compound (e.g. a halide) of one or more of these metals may be used.

Suitable catalysts comprising a zero-valent metal including supported (e.g. by carbon) transition metals such as Pd, Fe, Ni and Co.

Suitable metals for the catalysts comprising a metal oxide, a metal oxyhalide or a metal halide include transition metals, alkaline earth metals (e.g. Mg) and main group metals such as Al, Sn or Sb.

Alumina which has been modified by the addition of Cr, Cu, Zn, Mn, Au, Fe, Sn, Ta, Ti, Sb, In, Co, Ni, Mo, Ru, Rh, Pd and/or Pt and/or a compound (e.g. a halide) of one or more of these metals may be used.

A further group of preferred catalysts are supported (e.g. on carbon) lewis acid metal halides, including $TaX_5$, $SbX_5$, $SnX_4$, $TiX_4$, $FeCl_3$, $NbX_5$, $VX_5$, $AlX_3$ (wherein X=F or Cl). An oxide of a transition metal that has been modified by the addition of Cr, Mn, Au, Fe, Sn, Ta, Ti, Sb, In, Al, Co, Ni, Nb, Mo, Ru, Rh, Pd and/or Pt and/or a compound (e.g. a halide) of one or more of these metals may be used.

A preferred oxide of a transition metal is an oxide of Cr, Ti, V, Zr, or Fe. For example, chromia ($Cr_2O_3$) alone or chromia that has been modified by the addition of Zn, Mn, Mo, Nb, Zr, In, Ni, Al and/or Mg and/or a compound of one or more of these metals may be used. Catalysts based on chromia currently are particularly preferred. A preferred chromia-based catalyst is a zinc/chromia catalyst.

By the term "zinc/chromia catalyst" we mean any catalyst comprising chromium or a compound of chromium and zinc or a compound of zinc. Such catalysts are known in the art, see for example EP-A-0502605, EP-A-0773061, EP-A-0957074, WO 98/10862, WO 2010/116150, which documents are incorporated herein by reference.

Typically, the chromium or compound of chromium present in the zinc/chromia catalysts of the invention is an oxide, oxyfluoride or fluoride (preferably an oxide or oxyfluoride) of chromium.

The total amount of the zinc or a compound of zinc present in the zinc/chromia catalysts of the invention is typically from about 0.01% to about 25%, preferably 0.1% to about 25%, conveniently 0.01% to 6% zinc, and in some embodiments preferably 0.5% by weight to about 25% by weight of the catalyst, preferably from about 1 to 10% by weight of the catalyst, more preferably from about 2 to 8% by weight of the catalyst, for example about 4 to 6% by weight of the catalyst. In other embodiments, the catalyst conveniently comprises 0.01% to 1%, more preferably 0.05% to 0.5% zinc. It is to be understood that the amount of zinc or a compound of zinc quoted herein refers to the amount of elemental zinc, whether present as elemental zinc or as a compound of zinc.

The zinc/chromia catalysts used in the present invention may be amorphous. By this we mean that the catalyst does not demonstrate substantial crystalline characteristics when analysed by, for example, X-ray diffraction. Alternatively, the catalysts may be partially crystalline. By this we mean that from 0.1 to 50% by weight of the catalyst is in the form of one or more crystalline compounds of chromium and/or one or more crystalline compounds of zinc. If a partially crystalline catalyst is used, it preferably contains from 0.2 to 25% by weight, more preferably from 0.3 to 10% by weight, still more preferably from 0.4 to 5% by weight of the catalyst in the form of one or more crystalline compounds of chromium and/or one or more crystalline compounds of zinc.

The percentage of crystalline material in the catalysts of the invention can be determined by any suitable method known in the art. Suitable methods include X-ray diffraction (XRD) techniques. When X-ray diffraction is used the amount of crystalline material such as the amount of crystalline chromium oxide can be determined with reference to a known amount of graphite present in the catalyst (e.g. the graphite used in producing catalyst pellets) or more preferably by comparison of the intensity of the XRD patterns of the sample materials with reference materials prepared from suitable internationally recognised standards, for example NIST (National Institute of Standards and Technology) reference materials.

The zinc/chromia catalysts typically have a surface area of at least 50 m$^2$/g and preferably from 70 to 250 m$^2$/g and most preferably from 100 to 200 m$^2$/g before it is subjected to pretreatment with a fluoride containing species such as hydrogen fluoride or a fluorinated hydrocarbon. During this pre-treatment, which is described in more detail hereinafter, at least some of the oxygen atoms in the catalyst are replaced by fluorine atoms.

The amorphous zinc/chromia catalysts which may be used in the present invention can be obtained by any method known in the art for producing amorphous chromia-based catalysts. Suitable methods include co-precipitation from solutions of zinc and chromium nitrates on the addition of ammonium hydroxide. Alternatively, surface impregnation of the zinc or a compound thereof onto an amorphous chromia catalyst can be used.

Further methods for preparing the amorphous zinc/chromia catalysts include, for example, reduction of a chromium (VI) compound, for example a chromate, dichromate, in particular ammonium dichromate, to chromium (III), by zinc metal, followed by co-precipitation and washing; or mixing as solids, a chromium (VI) compound and a compound of zinc, for example zinc acetate or zinc oxalate, and heating the mixture to high temperature in order to effect reduction of the chromium (VI) compound to chromium (III) oxide and oxidise the compound of zinc to zinc oxide.

The zinc may be introduced into and/or onto the amorphous chromia catalyst in the form of a compound, for example a halide, oxyhalide, oxide or hydroxide depending at least to some extent upon the catalyst preparation technique employed. In the case where amorphous catalyst preparation is by impregnation of a chromia, halogenated chromia or chromium oxyhalide, the compound is preferably a water-soluble salt, for example a halide, nitrate or carbonate, and is employed as an aqueous solution or slurry. Alternatively, the hydroxides of zinc and chromium may be co-precipitated (for example by the use of a base such as sodium hydroxide or ammonium hydroxide) and then converted to the oxides to prepare the amorphous catalyst. Mixing and milling of an insoluble zinc compound with the basic chromia catalyst provides a further method of preparing the amorphous catalyst precursor. A method for making amorphous catalyst based on chromium oxyhalide comprises adding a compound of zinc to hydrated chromium halide.

The amount of zinc or a compound of zinc introduced to the amorphous catalyst precursor depends upon the preparation method employed. It is believed that the working catalyst has a surface containing cations of zinc located in a chromium-containing lattice, for example chromium oxide, oxyhalide, or halide lattice. Thus the amount of zinc or a compound of zinc required is generally lower for catalysts made by impregnation than for catalysts made by other methods such as co-precipitation, which also contain the zinc or a compound of zinc in non-surface locations.

The catalysts described herein (e.g. the chromia-based catalysts such as zinc/chromia catalysts) are typically stabilised by heat treatment before use such that they are stable under the environmental conditions that they are exposed to in use. This stabilisation is often a two-stage process. In the first stage, the catalyst is calcined by heat treatment in nitrogen or a nitrogen/air environment. The catalyst is then typically stabilised to hydrogen fluoride by heat treatment in hydrogen fluoride. This stage is often termed "prefluorination".

By careful control of the conditions under which these two heat treatment stages are conducted, crystallinity can be induced into the catalyst to a controlled degree.

In use, the catalysts described herein (e.g. the chromia-based catalysts such as the zinc/chromia catalysts) may be regenerated or reactivated periodically by heating in air at a temperature of from about 300° C. to about 500° C. Air may be used as a mixture with an inert gas such as nitrogen or with hydrogen fluoride, which emerges hot from the catalyst treatment process and may be used directly in any fluorination processes employing the reactivated catalyst.

The vapour phase catalytic dehydrochlorination may be carried out at a temperature of from about 200 to about 450° C. and at atmospheric, sub- or super-atmospheric pressure, preferably from about 0.1 to about 30 bara. Preferably, the catalytic dehydrochlorination is conducted at a temperature of from about 250 to about 400° C., such as from about 280 to about 380° C. or from about 300 to about 350° C.

The vapour phase catalytic dehydrochlorination preferably is carried out at a pressure of from about 0.5 to about 25 bara or about 1 to about 20 bara, such as from about 2 to about 18 bara (e.g. about 5 to about 20 bara or about 8 to about 18 bara or about 10 to about 15 bara).

HF is required for the fluorination of 1233xf in the process of the invention. The molar ratio of HF: 1233xf in the catalytic fluorination step is typically from about 1:1 to about 45:1, such as from about 1:1 to about 30:1, preferably from about 1.5:1 to about 30:1, such as from about 2:1 to about 20:1 or from about 3:1 to about 15:1. The inventors have unexpectedly found that these ranges strike a balance between the desirability to prevent and/or retard catalyst coking and residence time. If too little HF is used, coking increases. If too much HF is used, the residence time for a given reactor volume becomes shorter than desired.

If the catalytic dehydrochlorination and fluorination reactions are carried out in the same reactor, then both reactions are carried out in the presence of HF. When first and second reactors are used for the catalytic dehydrochlorination and fluorination reactions, then there need not be any HF present in the first reactor for the catalytic dehydrochlorination reaction. However, in some embodiments it is thought preferable to have HF present for the catalytic dehydrochlorination. Without being bound by theory, this is believed to prevent and/or retard catalyst coking.

If HF is present in the catalytic dehydrochlorination step, the molar ratio of HF:243db can fall within the ranges defined above for the molar ratio of HF:1233xf in the catalytic fluorination of 1233xf. In one aspect, however, less HF is used in the catalytic dehydrochlorination step compared to the catalytic fluorination step. Thus, the composition comprising 243db can additionally contain HF, typically in a molar ratio of HF:243db of from about 0.5:1 to about 40:1, such as from about 0.5:1 to about 20:1, preferably from about 1:1 to about 15:1, such as from about 1.5:1 to about 10:1 or from about 2:1 to about 8:1.

The contact time for the composition comprising 243db and HF with the catalyst in the catalytic dehydrochlorination step typically is from about 0.5 to about 200 seconds, such as from about 1 to about 150 seconds. Preferably, the contact time is from about 1 to about 100 seconds, such as from about 2 to about 80 seconds or from about 8 to about 60 seconds.

Turning now to the gas phase catalytic fluorination of the intermediate composition of the process of the invention, the HF in the intermediate composition typically is used to fluorinate 1233xf to 245cb. Preferably, the HF in the intermediate composition is the sole fluorinating agent for conversion of 1233xf to 245cb, although additional HF can be added to the process of the invention to facilitate this, particularly if a second reactor is used for the catalytic fluorination of 1233xf.

The catalyst used in the catalytic fluorination step may be any suitable catalyst that is effective to fluorinate 1233xf to 245cb. Preferred catalysts are bulk form or supported catalysts comprising activated carbon, a zero-valent metal, a metal oxide, a metal oxyhalide, a metal halide, or mixtures of the foregoing as described above in relation to the catalyst for the catalytic dehydrochlorination step.

Preferred catalysts for catalytic fluorination of 1233xf to 245cb are those which comprise chromia, alone or chromia that has been modified by the addition of Zn, Mn, Mo, Nb, Zr, In, Ni, Al and/or Mg and/or a compound of one or more of these metals. A preferred chromia-based catalyst for use in the catalytic fluorination of 1233xf to 245cb is a zinc/chromia catalyst. The same catalyst (e.g. a chromia-based catalyst) may be used for the catalytic dehydrochlorination and fluorination steps.

The vapour phase catalytic fluorination step may be carried out at a temperature of from about 200 to about 450° C. and at atmospheric, sub- or super-atmospheric pressure, preferably from about 0.1 to about 30 bara. Preferably, the vapour phase catalytic fluorination is conducted at a temperature of from about 250 to about 420° C., such as from about 280 to about 400° C. or from about 300 to about 380° C. (e.g. from about 330 to about 380° C.)

The vapour phase catalytic fluorination preferably is carried out at a pressure of from about 0.5 to about 25 bara or about 1 to about 20 bara, such as from about 2 to about 20 bara (e.g. about 5 to about 20 bara or from about 10 to about 15 bara).

The contact time for the for the composition comprising 1233xf, HCl and HF with the catalyst in the catalytic fluorination step typically is from about 0.5 to about 200 seconds, such as from about 1 to about 150 seconds. Preferably, the contact time is from about 1 to about 100 seconds, such as from about 2 to about 80 seconds or from about 5 to about 50 seconds.

245cb is a useful starting material for the manufacture of 1234yf. Accordingly, the process of the invention further comprises feeding 245cb into a dehydrofluorination reactor to produce a dehydrofluorination product comprising 2,3,3,3-tetrafluoropropene (1234yf) and HF.

The dehydrofluorination of 245cb may be carried out in the vapour and/or liquid phase and typically is carried out at a temperature of from about −70 to about 1000° C. (e.g. 0 to 450° C.). The dehydrofluorination may be carried out at atmospheric sub- or super atmospheric pressure, preferably from about 0.1 to about 30 bara.

The dehydrofluorination may be induced thermally, may be base-mediated and/or may be catalysed by any suitable catalyst. Suitable catalysts include metal and carbon based catalysts such as those comprising activated carbon, main group (e.g. alumina-based catalysts) and transition metals, such as chromia-based catalysts (e.g. zinc/chromia), lewis acid metal halides or zero-valent metal catalysts. One preferred method of effecting the dehydrofluorination of the compound of 245cb to produce 1234yf is by contacting with a metal-based catalyst, such as a chromia-based (e.g. zinc/chromia) catalyst.

Preferably, the 245cb is catalytically dehydrofluorinated to 1234yf in the gas phase.

243db is commercially available (e.g. from Apollo Scientific Ltd, UK). Alternatively, 243db may also be prepared via a synthetic route starting from the cheap feedstocks carbon tetrachloride (CCl4) and ethylene (see the reaction scheme set out below). These two starting materials may be telomerised to produce 1,1,1,3-tetrachloropropane (see, for example, J. Am. Chem. Soc. Vol. 70, p2529, 1948, which is incorporated herein by reference) (also known as HCC-250fb, or simply 250fb).

250fb may then be fluorinated to produce 3,3,3-trifluoropropene (1243zf) and/or 1,1,1- trifluoro-3-chloropropane (253fb) (e.g. using HF, optionally in the presence of a chromiacontaining catalyst, preferably a zinc/chromia catalyst as described herein). Dehydrohalogenation of 1,1,1-trifluoro-3-chloropropane (e.g. using NaOH or KOH or in the vapour phase) produces 3,3,3-trifluoropropene (1243zf).

1243zf may then be readily halogenated, such as chlorinated (e.g. with chlorine) to produce 1,1,1-trifluoro-2,3-dichloropropane (243db). This reaction scheme is summarized below.

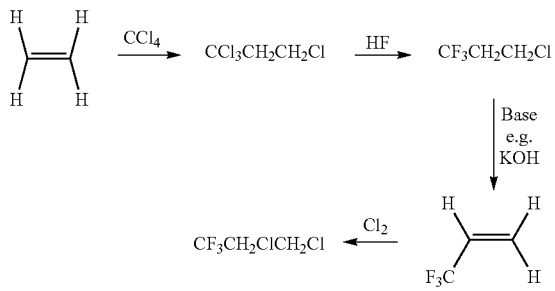

The preparation of 243db outlined above is described in more detail in WO 2010/116150 and WO 2009/125199, which are incorporated herein by reference.

Embodiments of the present invention will now be described with reference to the following non-limiting examples and drawings:

DETAILED DESCRIPTION

Figure 1:
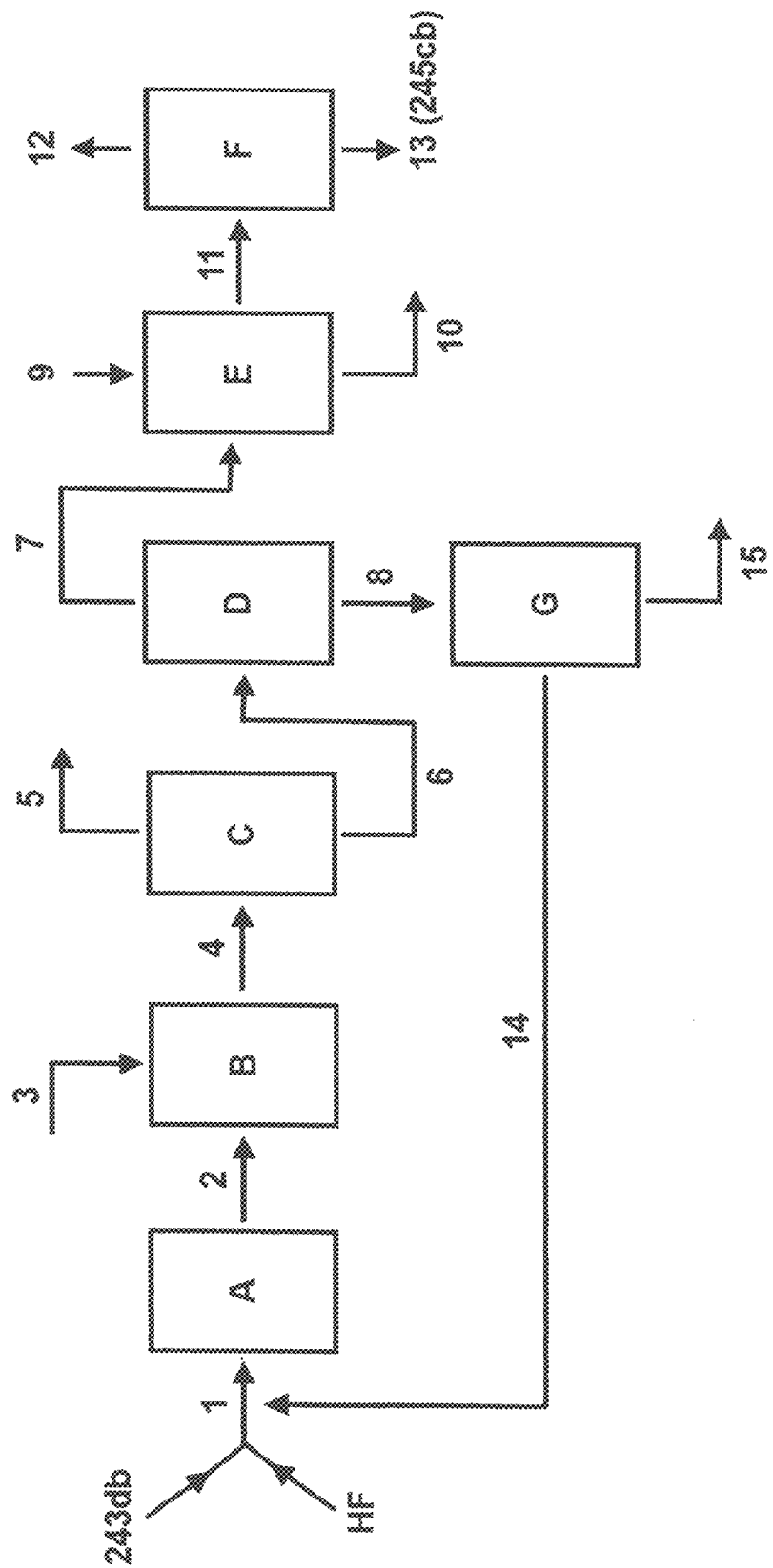
FIG. 1 shows a schematic process flow sheet in accordance with the invention.

FIG. 1 illustrates a process design in accordance with the invention. A composition (1) comprising 243db and HF is introduced into a first reactor (A) in which gas phase catalytic dehydrochlorination occurs to produce an intermediate composition (2) comprising 1233xf, HF and HCl. The intermediate composition may further contain unreacted 243db and, in certain embodiments, by-products such as 245cb and 1234yf.

The intermediate composition (2) is fed directly to a second reactor (B), as is a co-feed (3) of air, and gas phase catalytic fluorination of the intermediate composition (2) occurs in the second reactor (B) to produce a reactor product composition (4) comprising 245cb, HF, HCl and air. The reactor product composition may further contain unreacted 1233xf and, in certain embodiments, unreacted 243db and by-products such as 1234yf.

In a preferred embodiment, the reactor product composition (4) is separated at separation step (C) into a stream (5) comprising HCl and air and a stream (6) comprising 245cb and HF. An advantage of the use of the co-feed of air in the process of the invention is that it can be readily separated from the reactor product composition together with HCl. Preferably, this is achieved by distillation, with the stream (5) comprising HCl and air being taken off the top of a distillation column (e) and the stream (6) comprising 245cb and HF being taken off the bottom of the distillation column (e). The stream (6) typically contains any other components present, such as unreacted 243db, 1233xf and/or 1234yf.

In the embodiment illustrated by FIG. 1, the stream (6) comprising 245cb and HF is separated at separation step (D) into a 245cb-rich stream (7) and a HF-rich stream (8). Preferably, this is achieved by distillation, with the 245cb-rich stream (7) being taken off the top of a distillation column (D) and the HF-rich stream (8) being taken off the bottom of the distillation column (D). The 245cb-rich stream (7) typically also contains any relatively light organic components present, such as 1234yf. The HF-rich stream (8) typically also contains any relatively heavy organic components present, such as 1233xf.

Preferably the 245cb-rich stream (7) is subjected to a scrubbing step (E) in which any residual HF (and/or indeed any residual HCl) is substantially removed from the 245cb-rich stream to produce a 245cb-rich stream (11) substantially free from HF (and/or substantially free from HCl). Typically, this step (E) involves contacting the 245cb-rich stream (7) with water and/or or with a source of aqueous acid and/or or with a source of aqueous alkali, generally represented in FIG. 1 as stream (9), to generate the 245cb-rich stream (11) substantially free from HF and one or more spent scrubbing streams (10). By substantially free from HF, we include the meaning of less than 100 ppm, preferably less than 50 ppm, 40 ppm, 30 ppm, 20 ppm, 10 ppm, 5 ppm 4, ppm, 3 ppm, 3 ppm or less than 1 ppm. In a preferred embodiment, the 245cb-rich stream (11) is subjected to a separation step (F) in which the 245cb is further separated from any further organic components present (e.g. fluorocarbons such as 1234yf) to produce a substantially pure 245cb product (13). Preferably, this separation step (F) comprises one or more distillation steps. By substantially pure 245cb product (13), we include the meaning of greater than 95%, 98%, 99% pure, preferably greater than 99.5%, 99.8% or 99.9% pure, on a molar basis.

In a preferred embodiment, the HF in the HF-rich stream (8) is recycled to the catalytic dehydrochlorination of the composition comprising 243db and HF. As shown in FIG. 1, preferably, the HF-rich stream is subjected to a separation step (G) in which the HF-rich stream (8) is separated into an HF stream (14) and an organic stream (15). The HF stream is recycled to the composition (1) comprising 243db and HF which enters the first reactor (A) in which gas phase catalytic dehydrochlorination occurs. In a preferred aspect, the separation step (G) comprises a phase separator.

EXAMPLE 1

A series of catalysts (see Table 1 below) were screened for 243db dehydrochlorination. The test catalysts were ground to 0.5-1.4 mm and 2 mL was charged to an Inconel 625 reactor (0.5" OD×32 cm). The catalysts were pre-dried at 200° C. for at least 2 hours under a flow of N2 (60 ml/min). All the catalysts shown, except activated carbon, were pre-fluorinated as follows. HF at 30 ml/min was passed over the catalyst along with 60 ml/min nitrogen at 300° C. for one hour. The nitrogen was directed to the reactor exit leaving neat HF passing over the catalyst. The temperature was slowly ramped to 360° C. and held for hours before reducing to 250° C. All the experiments were run at atmospheric pressure and at the temperatures indicated. The 243db flow was 2 ml/min with activated carbon catalyst and ranged from 0.5 to about 1 ml/min for the remaining catalysts. All experiments were conducted with an HF flow in excess of the 243db flow, except for the activated carbon catalyst runs, in which no HF was used. Reactor off-gas was sampled scrubbing through deionised water and analysed by gas chromatography. The 243db conversion and selectivity to 1233xf are shown in Table 1.

TABLE 1

Experimental results for 243db dehydrochlorination

| Catalyst | Temperature ° C. | 243db Conversion % | 1233xf selectivity % |
|---|---|---|---|
| 2% Zn/Chrome | 250 | 98.22 | 74.79 |
|  | 300 | 100.00 | 42.28 |
|  | 350 | 100.00 | 68.74 |
| 4% Zn/Chrome | 250 | 99.18 | 81.80 |
|  | 300 | 98.47 | 77.42 |
|  | 350 | 100.00 | 70.80 |
| 6% Zn/Chrome | 250 | 94.94 | 65.55 |
|  | 300 | 100.00 | 33.81 |
|  | 350 | 100.00 | 71.30 |
| 8% Zn/Chrome | 250 | 89.06 | 60.20 |
|  | 300 | 100.00 | 82.93 |
|  | 350 | 100.00 | 72.72 |
| Chrome | 250 | 56.69 | 46.72 |
|  | 300 | 98.93 | 83.35 |
|  | 350 | 100.00 | 72.31 |

TABLE 1-continued

Experimental results for 243db dehydrochlorination

| Catalyst | Temperature ° C. | 243db Conversion % | 1233xf selectivity % |
|---|---|---|---|
| 5% In/Chrome | 250 | 98.64 | 81.36 |
|  | 300 | 100.00 | 68.23 |
|  | 350 | 100.00 | 52.65 |
| 6% Zn/Chrome | 250 | 96.51 | 85.17 |
|  | 300 | 100.00 | 69.18 |
|  | 350 | 100.00 | 72.19 |
| Zn/Chrome | 250 | 95.64 | 82.78 |
|  | 300 | 100.00 | 71.90 |
|  | 350 | 100.00 | 70.47 |
| Zn/Chrome | 250 | 91.76 | 81.19 |
|  | 300 | 100.00 | 77.74 |
|  | 350 | 100.00 | 70.90 |
| Chrome | 250 | 93.60 | 80.31 |
|  | 300 | 100.00 | 48.69 |
|  | 350 | 100.00 | 38.38 |
| Mo/Chrome | 250 | 93.24 | 80.25 |
|  | 300 | 100.00 | 54.87 |
|  | 350 | 100.00 | 26.63 |
| Ni/Chrome | 250 | 100.00 | 84.05 |
|  | 300 | 100.00 | 39.93 |
|  | 350 | 100.00 | 24.93 |
| Nb/Chrome | 250 | 98.94 | 86.54 |
|  | 300 | 100.00 | 56.26 |
|  | 350 | 100.00 | 34.94 |
| Alumina | 250 | 29.10 | 38.87 |
|  | 300 | 73.37 | 69.75 |
|  | 350 | 98.37 | 90.94 |
| 0.5% Pt/Alumina | 250 | 44.53 | 48.63 |
|  | 300 | 87.56 | 82.09 |
|  | 350 | 100.00 | 96.02 |
| Fe/Alumina | 250 | 22.45 | 39.46 |
|  | 300 | 52.57 | 71.90 |
|  | 350 | 80.99 | 84.47 |
| 20% Cr/Alumina | 250 | 43.85 | 44.17 |
|  | 300 | 97.71 | 79.58 |
|  | 350 | 98.56 | 77.88 |
| 50% Cr/Alumina | 250 | 45.73 | 42.68 |
|  | 300 | 100.00 | 79.86 |
|  | 350 | 100.00 | 72.95 |
| Zn/Cu/Alumina | 250 | 40.73 | 47.65 |
|  | 300 | 74.85 | 71.21 |
|  | 350 | 65.17 | 64.86 |
| 0.5% Pd/Carbon | 250 | 100.00 | 99.19 |
|  | 300 | 100.00 | 98.38 |
|  | 350 | 100.00 | 85.78 |
| activated carbon | 175 | 46.06 | 99.13 |
|  | 200 | 98.46 | 97.32 |
|  | 300 | 99.07 | 97.02 |

All of the catalysts tested were found to be effective at converting 243db to 1233xf, particularly activated carbon.

EXAMPLE 2

6.07 g of a Indium-doped chromia catalyst was dried over 72 hours under nitrogen (80 ml/min) at 250° C. and 3 barg. This was followed by two-stage pre-fluorination of the catalyst. In stage 1, the catalyst was exposed to nitrogen (80 ml/min) and HF (4 ml/min) at 250° C. and 3 barg up until 4 hours from HF breakthrough, at which time the temperature was increased at 25° C./min to 300° C. and held for 16 hours. In stage 2, nitrogen flow was reduced stepwise until it was switched off, and the temperature was increased at 25° C./min to 380° C. and held for 10 hours. The HF flow was stopped and replaced with nitrogen (40 ml/min) and the temperature reduced to 250° C. ready for use.

Figure 2:
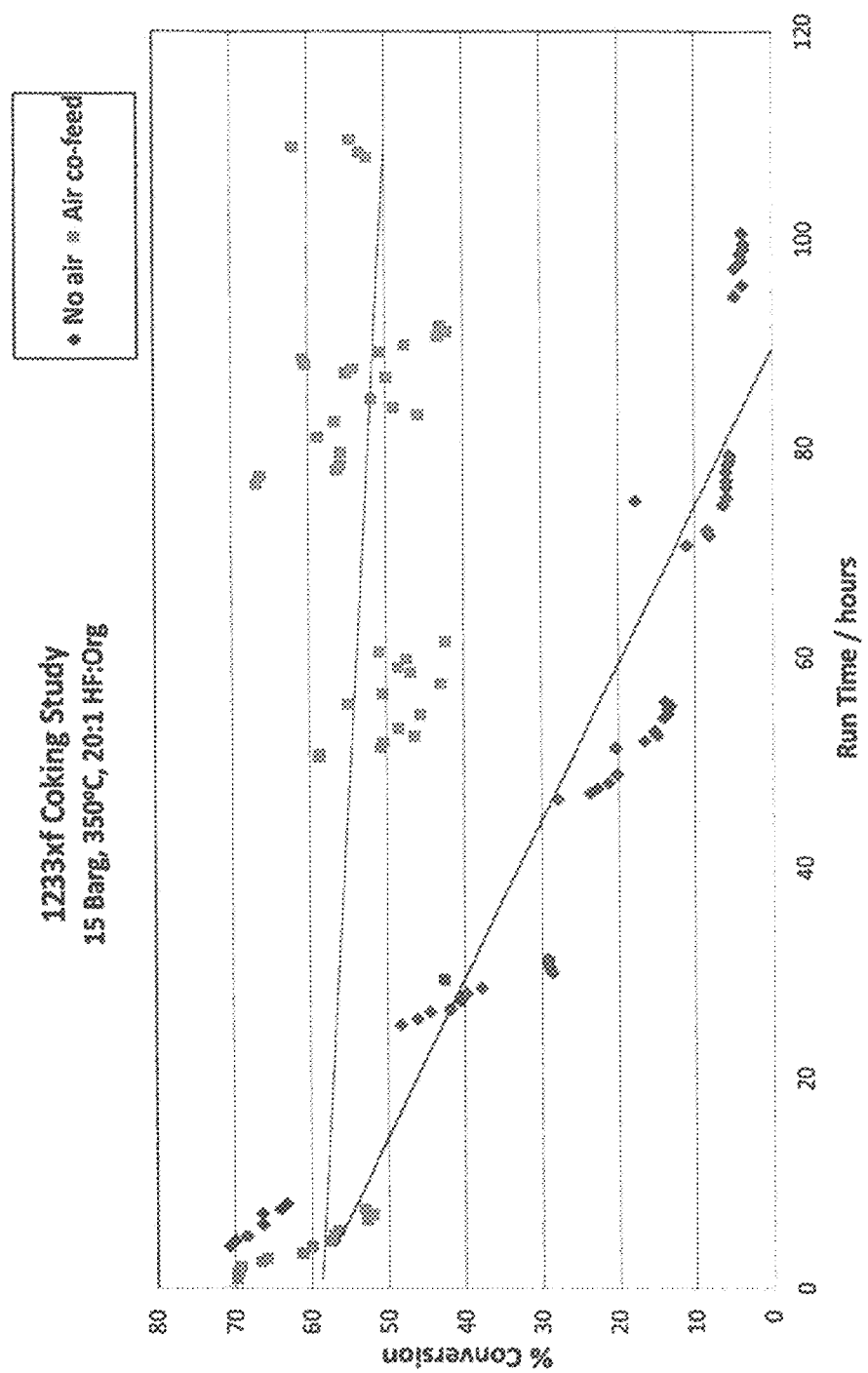
FIG. 2 shows the results of a coking study in which conversion is plotted over time for the fluorination of 1233xf in accordance with the invention.

1233xf was co-fed with HF over the catalyst without an air co-feed (cycle 1) and with an air co-feed (cycle 2) for about 100 hours at 350° C. and 15 barg. Reactor off-gas was analysed by GC. Monitored catalyst regeneration was used to measure the average coke levels in the catalyst after use. The results are shown in Table 2 below and illustrated in FIG. 2.

TABLE 2

Experimental conditions and results for two ageing runs

| | | | | | | Conversion | | |
|---|---|---|---|---|---|---|---|---|
| | Cycle time | Coke levels | Target flows (ml/min) | | | Loss | Loss Hours | Loss rate |
| Cycle | (hrs) | (%) | HF | 1233xf | Air | (%) | | (5/hr) |
| 1 | 100.5 | 5.6 | 50 | 5 | — | 64.8 | 74 | 0.88 |
| 2 | 110 | 0.35 | 45 | 5 | 5 | 16.8 | 106 | 0.16 |

Both cycles were conducted at the same temperature and pressure, but the HF flow was reduced in cycle 2 to maintain contact time. Contact times for cycles 1 and 2 were 57 seconds and 65 seconds, respectively. As a result of the reduced HF flow on cycle 2 and the lower than target 1233xf flows, which were hard to control and lower than target, the HF:1233xf ratio differed slightly on the two cycles (average 20:1 for cycle 1 and 15:1 for cycle 2). The average 1233xf flow for cycle 1 was 3.2 ml/min and 3.5 ml/min for cycle 2.

Without air the majority of catalyst activity was lost after about 80 hours. The introduction of air significantly reduced the rate of catalyst deactivation (the activity loss after 100 hours was comparable with just 20 hours without air). Based on this conversion loss rate, cycle 2 would be expected to take 410 hours to reach the same conversion loss as cycle 1. The reduced rate of catalyst deactivation with air co-feed is in accordance with the catalyst coke levels measured.

The reaction selectively was also affected, total impurity levels approximately doubled with the co-feed of air compared to without air. Co-feeding air seemed to have a little impact on the 245cb:1234yf ratio though.

The concentration of air present was higher than desired because the 1233xf flow rate was, on average, lower than the targeted 5 ml/min. This was thought to be at least partially responsible for the decreased selectivity. For this reason, and based on the coke produced in cycle 1, a lower air concentration is believed to be desirable to achieve comparable reduced rates of catalyst deactivation without reducing conversion and 245cb selectivity. It was estimated that lower air flows, for example from about 0.5 ml/min to about 4.5 ml/min, preferably from about 1 to about 4 ml/min, such as from about 1.5 to 3.5 ml/min (all based on an actual 1233xf flow of 5 ml/min) would realise the surprising balance of reduced rates of catalyst deactivation combined with conversion selectivity to the desired 245cb product.

The invention is defined by the following claims.

We claim:

1. A process for preparing 1,1,1,2,2-pentafluoropropane (245cb) and 2,3,3,3-tetrafluoropropene (1234yf), the process comprising:
   gas phase catalytic dehydrochlorination of a composition comprising 1,1,1-trifluoro-2,3-dichloropropane (243db) to produce an intermediate composition comprising 3,3,3-trifluoro-2-chloro-prop-1-ene ($CF_3CCl=CH_2$, 1233xf), hydrogen chloride (HCl), or 1233xf, HCl and air; and
   gas phase catalytic fluorination with hydrogen fluoride (HF) of the intermediate composition to produce a reactor product composition comprising 245cb, 1234yf, HF, HCl and air;
   optionally wherein the process is carried out with a co-feed of air.

2. The process according to claim 1 wherein the dehydrochlorination step is carried out in a first reactor and the fluorination step is carried out in a second reactor.

3. The process according to claim 2 wherein the intermediate composition exits the first reactor and is fed directly to the second reactor.

4. A process for preparing 1,1,1,2,2-pentafluoropropane (245cb) and 2,3,3,3-tetrafluoropropene (1234yf), the process comprising:
   gas phase catalytic dehydrochlorination in a first reactor of a composition comprising 1,1,1-trifluoro-2,3-dichloropropane (243db) to produce an intermediate composition comprising 3,3,3-trifluoro-2-chloro-prop-1-ene ($CF_3CCl=CH_2$, 1233xf) and hydrogen chloride (HCl); and
   gas phase catalytic fluorination with hydrogen fluoride (HF) in a second reactor of the intermediate composition to produce a reactor product composition comprising 245cb, 1234yf, HF, HCl and air;
   optionally wherein the process is carried out with a co-feed of air to the second reactor.

5. The process according to claim 4 wherein the intermediate composition exits the first reactor and is fed directly to the second reactor.

6. The process according to claim 4 wherein the catalytic dehydrochlorination of 243db is carried out in the presence of HF and the intermediate composition further contains HF.

7. The process according to claim 6 wherein the composition comprising 243db additionally contains HF, with a molar ratio of HF:243db of from 0.5:1 to 40:1, or from 1:1 to 15:1.

8. The process according to claim 6 wherein the contact time for the composition comprising 243db and HF with the catalyst is from 0.5 to 200 seconds, or from 1 to 150 seconds, or from 1 to 100 seconds, or from 2 to 80 seconds, or from 8 to 60 seconds.

9. The process according to claim 2 wherein the molar ratio of HF:1233xf in the second reactor is from 1:1 to 45:1, or from 2:1 to 20:1 or from 3:1 to 15:1, or wherein an additional feed of HF is provided to the second reactor.

10. The process according to claim 2 wherein the contact time for the composition comprising 1233xf, HCl and HF with the catalyst is from 0.5 to 200 seconds, or from 1 to 150 seconds, or from 1 to 100 seconds, or from 2 to 80 seconds, or from 5 to 50 seconds.

11. The process according to claim 1 wherein the reactor product composition is separated into a stream comprising 245cb, 1234yf and HF and a stream comprising HCl and air.

12. The process according to claim 11 wherein the stream comprising 245cb, 1234yf and HF is separated into a 245cb-rich stream and a HF-rich stream.

13. The process according to claim 12 wherein the 245cb-rich stream contains 1234yf.

14. The process according to claim 12 wherein the HF-rich stream contains 1233xf.

15. The process according to claim 11 wherein the separation is achieved by distillation.

16. The process according to claim 11 wherein the 245cb-rich stream is subjected to a scrubbing step in which residual HF is substantially removed from the 245cb-rich stream to produce a 245cb-rich stream substantially free from HF.

17. The process according to claim 11 wherein the 245cb is separated from the 1234yf to provide a substantially pure 245cb product.

18. The process according to claim 17 wherein the separation is achieved by distillation.

19. The process according to claim 1 wherein the catalytic dehydrochlorination is carried out at a temperature of from 200 to 450° C. and a pressure of from 0.1 to 30 bara, or at a temperature of from 250 to 380° C. and a pressure of from 1 to 20 bara, or at a temperature of from 300 to 350° C. and a pressure of from 5 to 20 bara.

20. The process according to claim 1 wherein the catalytic dehydrochlorination is carried out in the presence of a bulk form or supported catalyst comprising activated carbon, a zero-valent metal, a metal oxide, a metal oxyhalide, a metal halide, or mixtures thereof.

21. The process according to claim 20 wherein the metal is a transition metal, an alkaline earth metal or aluminum.

22. The process according to claim 20 wherein the catalyst is based on chromia, or a zinc/chromia catalyst.

23. The process according to claim 1 wherein the catalytic fluorination is carried out at a temperature of from 200 to 450° C. and a pressure of from 0.1 to 30 bara, or at a temperature of from 250 to 420° C. and a pressure of from 1 to 20 bara, or at a temperature of from 300 to 380° C. and a pressure of from 5 to 20 bara.

24. The process according to claim 1 wherein the catalytic fluorination is carried out in the presence of a bulk form or supported catalyst comprising activated carbon, a zero-valent metal, a metal oxide, a metal oxyhalide, a metal halide, or mixtures thereof.

25. The process according to claim 24 wherein the metal is a transition metal, an alkaline earth metal or aluminum.

26. The process according to claim 24 wherein the catalyst is based on chromia, or a zinc/chromia catalyst.

27. The process according to claim 1 wherein the HF in the reactor product composition is at least partially recycled to the catalytic dehydrochlorination of the composition comprising 243db and HF.

28. The process according to claim 12 wherein the HF in the HF-rich stream is recycled to the catalytic dehydrochlorination of the composition comprising 243db and HF.

29. The process according to claim 28 wherein the HF-rich stream is separated into an HF stream and an organic stream, wherein the HF stream is recycled to the catalytic dehydrochlorination of the composition comprising 243db and HF.

* * * * *